(12) United States Patent
Njamfa

(10) Patent No.: US 9,297,682 B1
(45) Date of Patent: Mar. 29, 2016

(54) INLINE FLOW RATE METER WITH AUXILIARY FLUID INJECTION AND DETECTION

(71) Applicant: Serge Njamfa, Culver City, CA (US)

(72) Inventor: Serge Njamfa, Culver City, CA (US)

( * ) Notice: Subject to any disclaimer, the term of this patent is extended or adjusted under 35 U.S.C. 154(b) by 13 days.

(21) Appl. No.: 14/482,381

(22) Filed: Sep. 10, 2014

(51) Int. Cl.
*G01F 1/708* (2006.01)

(52) U.S. Cl.
CPC ........................... *G01F 1/708* (2013.01)

(58) Field of Classification Search
USPC ...................................... 73/861.05
See application file for complete search history.

(56) References Cited

U.S. PATENT DOCUMENTS 4,559,831 A * 12/1985 Prestele ............ A61M 5/16886
73/861.05
4,628,743 A * 12/1986 Miller, Jr. ............. G01F 1/7044
73/204.25
5,355,735 A * 10/1994 Miller ..................... G01F 1/708
73/861.05

* cited by examiner

*Primary Examiner* — Jewel V Thompson
(74) *Attorney, Agent, or Firm* — Joseph C. Andras; Myers Andras LLP

(57) ABSTRACT

A continuous, inline, flow rate measurement system for rapidly measuring a flow rate in an analytical instrument having a primary pump that outputs a primary fluid at the flow rate to be measured or verified. The flow rate measurement system includes an auxiliary pump that outputs an auxiliary fluid bubble having a detectable characteristic that is distinguishable from the primary fluid, a bubble injection system that injects a small portion of the auxiliary fluid into the conduit, and a bubble detection system for measuring the position of the auxiliary fluid bubble as a function of time based on a time of detecting the detectable characteristic of the auxiliary fluid, and a controller for converting the measured position of the auxiliary fluid bubble as a function of time into a volumetric flow rate based on a known volume of the conduit.

18 Claims, 6 Drawing Sheets

EXEMPLARY HPLC SYSTEM

EXEMPLARY HPLC SYSTEM

PRIMARY PUMP USED IN AN EXEMPLARY HPLC SYSTEM

FLOW RATE MEASUREMENT DEPLOYED IN AN EXEMPLARY HPLC SYSTEM

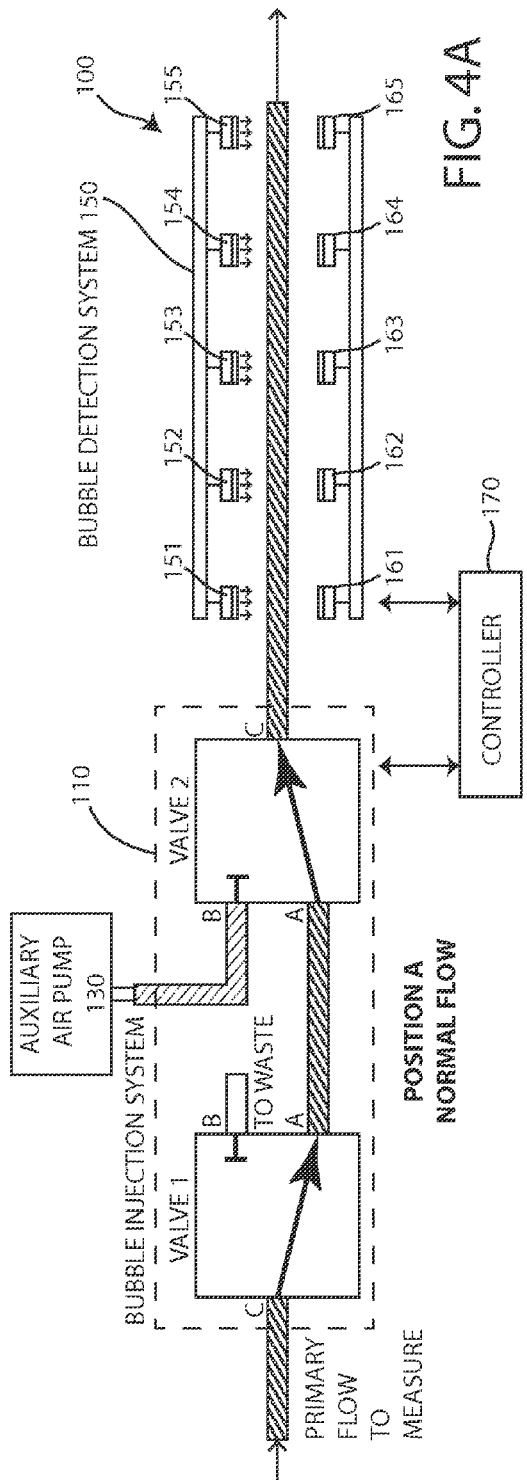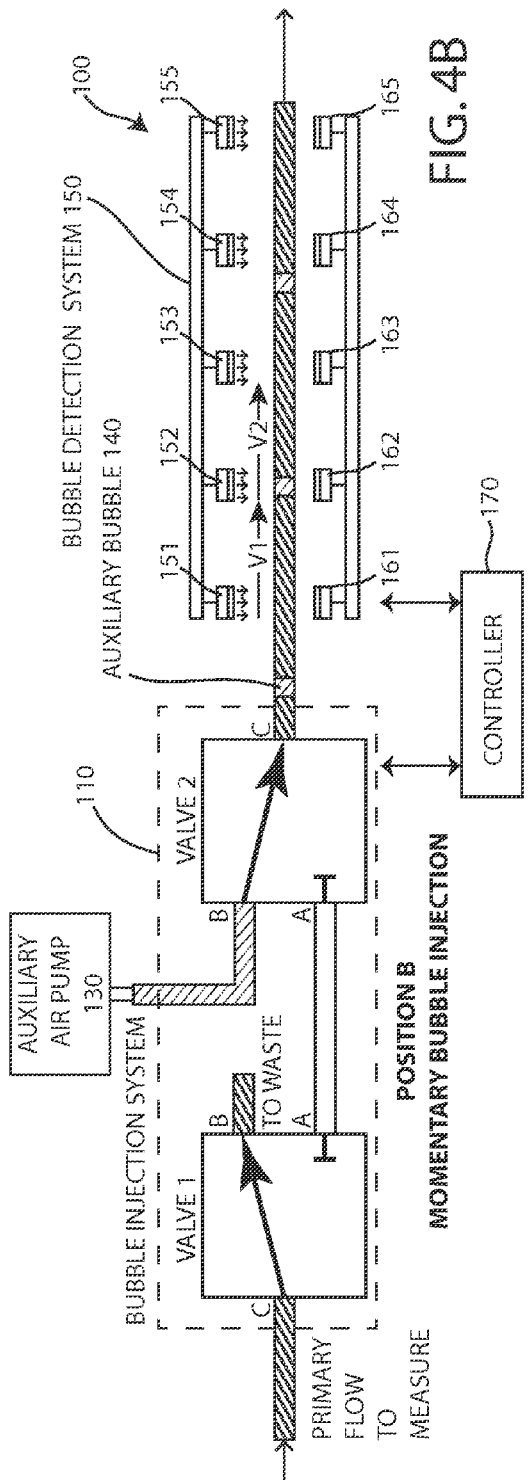

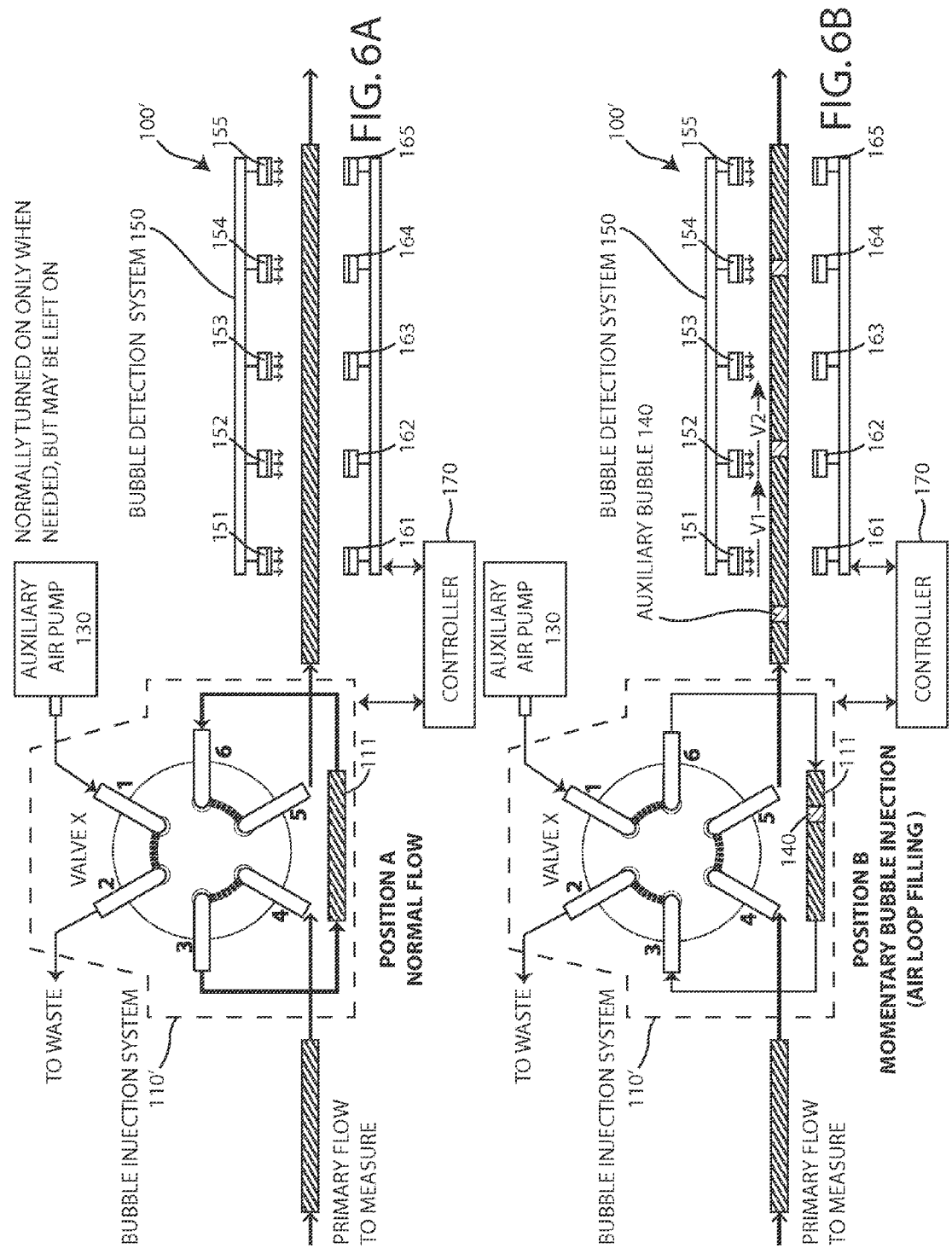

INLINE FLOW RATE METER WITH AUXILIARY FLUID INJECTION AND DETECTION

BACKGROUND OF THE INVENTION

1. Field of the Invention

This application relates generally to analytical devices such as liquid chromatography systems and, more particularly, to an inline flow rate meter with auxiliary fluid injection and detection for measuring volumetric flow rates.

2. Description of the Related Art

Chromatography is used for separating a sample into its various components. In more detail, chromatography is a group of analytical methods for taking a sample (e.g. a complex mixture) and separating its component substances, or analytes, from one another. In general, analytical chromatography is used to determine the existence and sometimes the concentration of analytes in a sample.

All chromatography systems involve two phases (states) of matter; a stationary phase and a mobile phase that carries the mixture through or past the stationary phase. The stationary phase is a solid and the mobile phase is a fluid, i.e. a liquid or a gas. As the mobile phase containing the mixture moves through the stationary phase, the components separate from one another because the components have different affinities for the two phases and thus move through the system at different rates. A component with a high affinity for the mobile phase moves relatively quickly through the chromatographic system, whereas one with a high affinity for the solid phase moves more slowly. The fast moving components, therefore, will be separated from the slow moving components.

Paper Chromatography

Paper chromatography is a simple and, to the layman, most familiar form of chromatography. It is very visual in nature. In paper chromatography, the stationary phase is usually a strip of porous paper, i.e. filter paper. A small dot or line of the mixture to be separated is placed on the paper strip, near its lower end, and then the paper strip is dipped into a liquid solvent (the mobile phase) that travels up the paper through capillary action—like a wick. The mobile phase reaches the mixture and then carries the mixture's different components along the paper. How fast each component moves along the paper depends on its relative affinity for the mobile and stationary phases. The components with the weakest attraction for the paper or greater affinity for the mobile phase travel faster than those that cling to the paper. For example, if the mobile phase is more polar than the stationary phase, the more polar components of the mixture will tend to move more quickly than the less polar components. The resulting separation visually shows the mixture's separate components.

Column-Based Liquid Chromatography

Column-based Liquid chromatography, usually just called liquid chromatography or LC, is a more complex method of chromatography where the stationary phase is contained within a so-called "column" rather than consisting of a sheet of paper. The mobile phase is usually a liquid solvent of one kind or other and the mixture to be analyzed is dissolved in or carried by the solvent.

Classic liquid chromatography is based on gravity. In such case, the column is a vertical tube that has been packed with a bed of suitable powder (the stationary phase) and gravity is the force that moves the mobile phase through the column. The components of the mixture that are carried through the column by the mobile phase can be visually identified if the column is clear and the components are differently colored, or they can be analyzed based on suitable measurements and the time that each component takes to travel through and exit the column.

Liquid chromatography often uses a pump in lieu of gravity. In a pump-based system, a primary pump is used to force the mobile phase through the column. In such case, the column may actually be horizontal. As the mobile phase exits the far end of the column, it transports the mixture's components out of the column, one after the other, and into a detector of one kind or another for compositional analysis based on measurement and the time that the component took to travel through and exit the column.

High Performance Liquid Chromatography (HPLC)

High Performance Liquid Chromatography (HPLC), sometimes aptly called high-pressure liquid chromatography, is another type of column-based chromatography that, like all forms of chromatography, uses a mobile phase to move the mixture through a stationary phase. HPLC provides high resolution results in a comparatively short period of time by using a relatively high pressure pump to force the solvent (the mobile phase) through relatively small diameter columns (e.g. 4.6 mm) that are packed with a stationary phase of very small particles (e.g. 1.5, 3, 5, or 10 µm, or microns) having a narrow particle size distribution (e.g. within 10% of the mean).

In order to achieve a separation using HPLC, we need to create a flow of mobile phase through the column. To do this, tubing is connected to the end of the column. Because of the small size of the particles in the column, the fluid needs to be pushed through the column at high pressure to get a reasonable flow rate.

In HPLC, as with traditional liquid chromatography, the stationary phase consists of a column (i.e. a metal tube) that has been packed with a solid (e.g. silica particles) and the unknown mixture to be analyzed is mixed with a mobile phase that consists of a suitable solvent. In HPLC, the liquid forming the mobile phase is forced through the column with high pressure pumps. If one regards the high pressure pump as a primary pump, then its liquid output is a primary fluid.

The solvent used is a matter of choice. HPLC usually involves a mixture of solvents that are chosen to provide the correct amount of polarity for a given separation. For example, the mixture could be comprised of 60% acetonitrile or ACN (less polar) and 40% water (very polar).

The typical HPLC pump produces a very high pressure, e.g. 15,000 Kilopascals (~2,175 PSI) or 150× that of the atmosphere (standard atmospheric pressure is about 101.325 kPA). In HPLC, if a single sample is to be analyzed, a hypodermic syringe is usually used to inject the sample into the solvent stream via an injection port. Alternatively, and given the appropriate equipment, the operator can analyze several samples that are pre-injected into a plurality of vials that are then placed in a so-called autosampler that will run them in order without human intervention.

FIG. 1 is a simplified diagram of an exemplary HPLC system 10. As shown, the HPLC system 10 comprises a reservoir 20 containing a liquid solvent 21, a primary pump 30 that produces a primary fluid flow within a conduit that begins with tube 32, a sample vial containing a sample 41, an injector 50, a separation column 60, a detector 70, and a waste reservoir 80. In this particular system 10, the detector 70 is configured to display the chromatogram on a computer 71. In the drawing, the output paths of the injector 50, column 60, and detector 70 are identified with reference numbers 52, 62, and 72, respectively. In general, a conduit for transporting the fluid through the analytical instrument comprises the combined flow path through segments 32, 52, 62, and 72.

FIG. 2 illustrates an exemplary primary pump 30. The illustrated pump 30 uses a reciprocating piston that is driven by a motor, and a pair of check valves, but the pump 30 can be of any suitable construction. The pump 30, however, must be able to maintain accurate flow rates for accurate analysis in the HPLC system 10.

In operation, the pump 30 draws solvent 21 from the reservoir 20 via tube 22 and outputs a high pressure, primary fluid flow via tube 32. The injector 50 functions to place the sample 41 into the high pressure flow 32 so that the sample is transported to the column 60 as a homogenous, low-volume plug within tube 52. The pump 30 continues to force the solvent 21 and sample 41 into one end of the column 60 and, ultimately, the solvent 21 and separated components of the sample 41 emerge from the other end of the column 60 at which point the separated components of the sample 41 are analyzed by a suitable detector 70 that generates a chromatogram that is indicative of the components present. One common type of detector uses UV light. Another type of detector measures refractive index. There are many different kinds. Eventually, the solvent 21 and components of the sample 41 are dispensed into the waste reservoir 80.

The time that it takes a component to travel from the injection port 50, through the column 60, and then reach the detector 70 is called its "retention time" and it can be used to help identify the components and overall mixture 41. The HPLC system 10 typically produces a chromatograph that shows peaks of some characteristic response being measured by the detector 70, the peaks being horizontally spread out along the abscissa (X-axis) as a function of retention time.

The retention time is a function of the component's interaction with the stationary phase, the composition of the solvent, and of special significance to this invention, the flow rate of the mobile phase or primary fluid flow. In order to produce an accurate HPLC chromatograph based on retention time, the flow rate must be accurately known and maintained.

Existing Flow Rate Measurement Techniques

The pump used in an HPLC system must consistently provide accurate, stable, and known flow rates. In certain situations, the operator can directly verify the flow rates for different flow rate settings through actual time and volume measurements. This is done by diverting the flow of solvent and by measuring the amount of time required to collect a known amount of solvent. The solvent can be diverted for measurement on the upstream or downstream side of the column. In either case, the user temporarily diverts the flow of solvent into a volumetric measuring device (e.g. a volumetric flask, a graduated cylinder, or a pipette) and uses a timer to measure how much fluid flows into the measuring device in a given amount of time. For example, if one is trying to verify the flow-rate accuracy at 2 mL/min, one could use a stopwatch to measure the time that it takes to collect 25 mL of effluent that is diverted into a 25 mL volumetric flask. At exactly 2 mL/min, it would take 12.5 minutes to fill the flask. For reasonable operation, one would expect to have a flow rate accuracy of +/−1% of the set flow rate.

Diverted flow rate measurements detrimentally take the system offline and often take more time than desired.

Moreover, diverted flow rate measurements are only suitable for relatively high flow rates. The lowest flow rate that can reasonably be measured and verified with a direct measurement technique is about 1 ml/minute. However, certain HPLC applications often require verification of very low flow rates that are a few orders magnitude lower.

Another technique for measuring flow rate is based on temperature as disclosed, for example, in U.S. Pat. No. 6,813,944 assigned to Sensiron AG. The device disclosed in the 944 patent includes a heat source and two temperature sensors that correlate the flow rate with a measured temperature gradient. In essence, it is a parametric measurement of flow rate, and not a direct measurement.

There remains a need, therefore, for an improved flow meter that operates quickly, does not require diversion, does not interrupt the analytical process, directly measures the flow rate, and can be effectively used with very low flow rates.

DESCRIPTION OF THE DRAWINGS

FIG. 4A shows an inline flow rate measurement system 100 according to a first preferred embodiment of the invention having a bubble injection system formed from two valves, Valve 1 and Valve 2, and with Valve 1 and Valve 2 in the NORMAL FLOW position;

FIG. 4B shows the inline flow rate measurement system 100 of FIG. 3 with Valve 1 and Valve 2 in the MOMENTARY BUBBLE INJECTION position to inject an air bubble 140 into the flow;

FIG. 6A shows an inline flow rate measurement system 100' according to a second preferred embodiment of the invention having a bubble injection system formed from one valve, Valve X, and a fluid loop, and with Valve X in the NORMAL FLOW position;

FIG. 6B shows the inline flow rate measurement system 100' of FIG. 6A with Valve X in the MOMENTARY BUBBLE INJECTION position to inject an air bubble 140 into the fluid loop and, ultimately, into the flow;

DETAILED DESCRIPTION OF THE PREFERRED EMBODIMENTS

The following is a detailed description of various embodiments of a flow rate measurement system 100 that beneficially operates on demand, in real time, and in an inline situation. The embodiments that are illustrated and described herein involve just some of the many possible valves injection systems for injecting an auxiliary fluid into a primary fluid flow, and just some of the many possible bubble detection systems for directly measuring the flow rate of the primary fluid based on the position detection of the injected bubble and the known volume of fluid between detection points.

Figure 1:
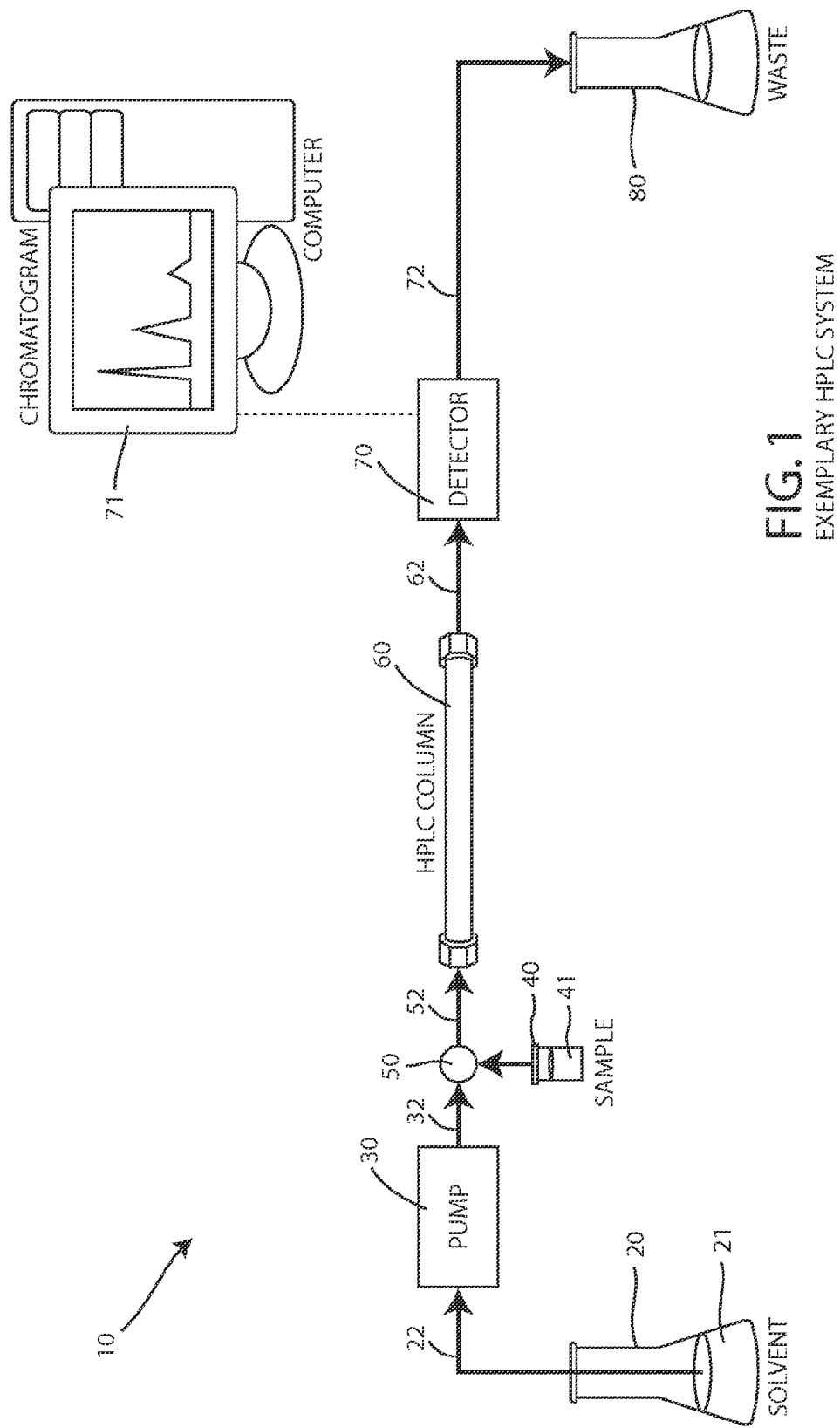
FIG. 1 is a schematic diagram of an analytical instrument comprising an HPLC system 10 that requires accurate and stable verification of the flow rate generated by a primary pump 30.
Figure 2:
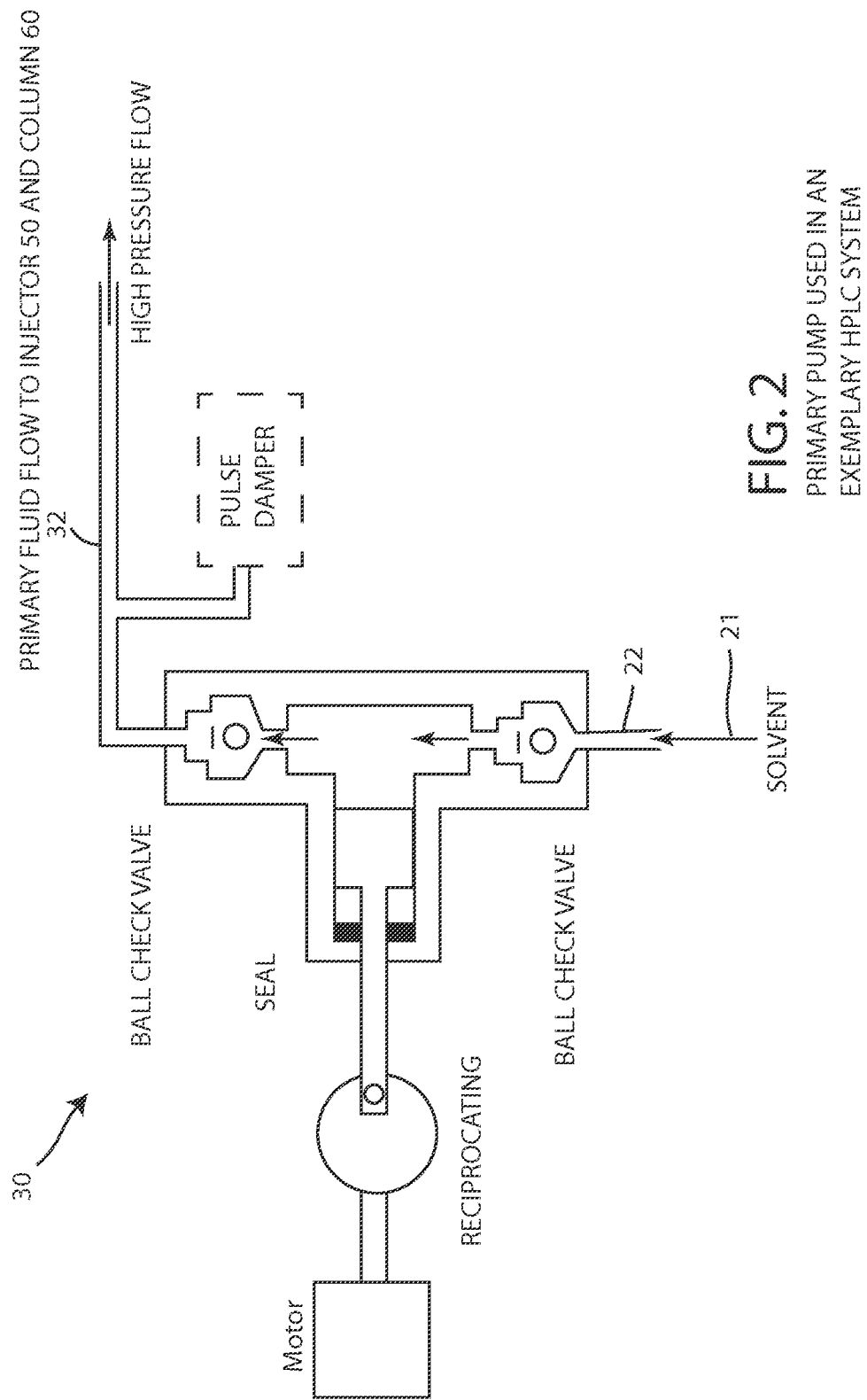
FIG. 2 shows an exemplary construction for the primary pump 30 used in an HPLC system 10 like that of FIG. 1.
Figure 3:
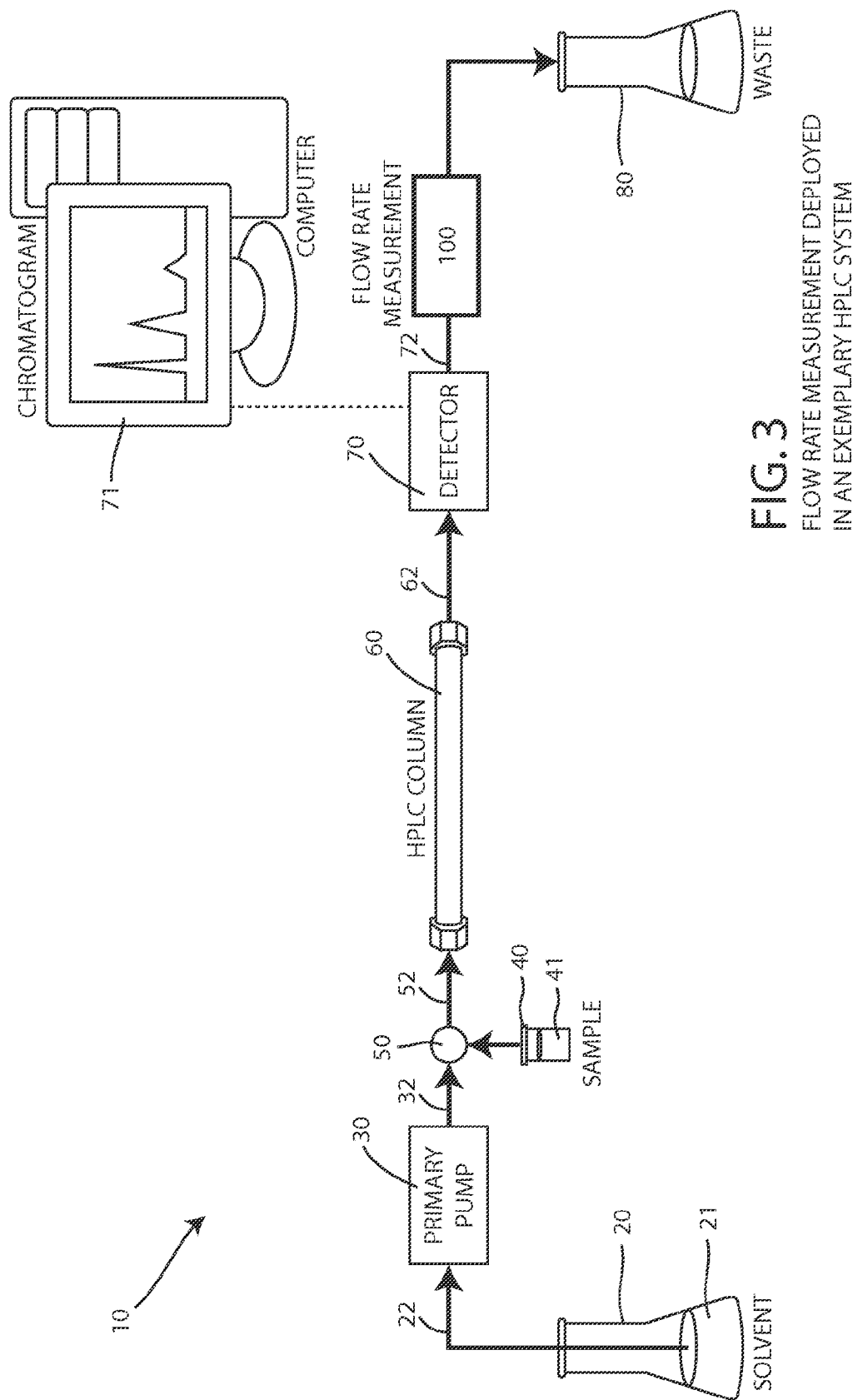
FIG. 3 shows an HPLC system 10 that incorporates an inline flow rate measurement system 100 according to various embodiments of this invention.
Figure 5A:
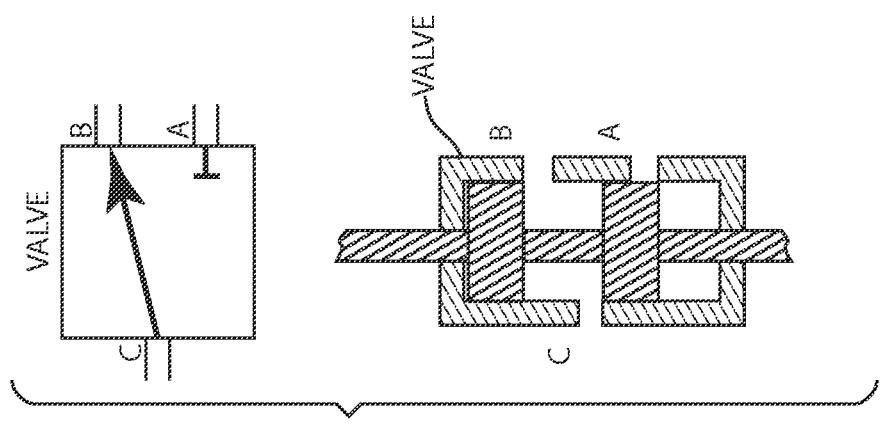
FIGS. 5A and 5B show one of many possible valve mechanics for implementation of Valve 1 and Valve 2 used in the inline flow rate measurement system 100 of FIGS. 4A and 4B, the plunger being to one side to connect the common port to port A in FIG. 5A and to the opposite side to connect the common port to port B in FIG. 5B.
Figure 5B:
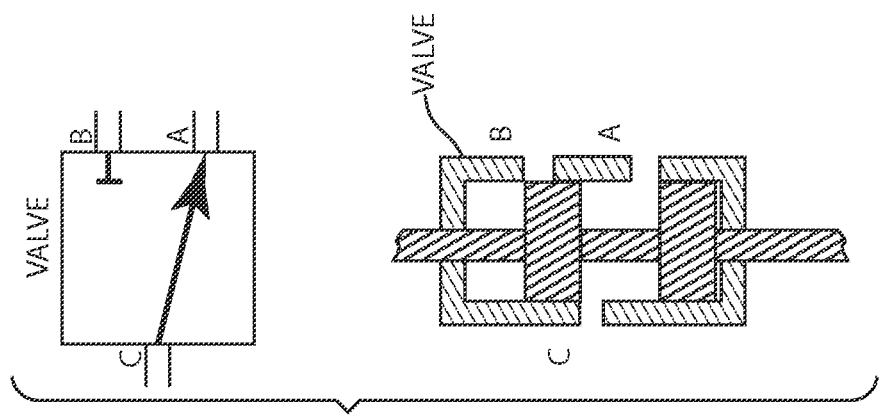

FIG. 3 shows a flow rate measurement system 100 integrated inline into an HPLC system 10 like that of FIG. 1. It should be understood, however, that a flow rate measurement system 100 according to the present invention could be incorporated into any analytical instrument that would benefit from the measurement or verification of an associated flow rate.

The flow rate measurement system 100 could theoretically be placed most anywhere desired along the analytic fluid path. When used in an HPLC system 10 having a column 60, the system 100 is preferably placed downstream of the column 60 so that bubbles are not introduced into the column 60.

First Preferred Embodiment

FIGS. 4A and 4B depict a first preferred embodiment of a flow rate measurement system 100 that uses a bubble injection system 110, a bubble detection system 150, and a suitable controller 170. As shown in FIG. 3, a primary fluid (e.g. solvent 21) is normally output by the primary pump 30 and is flowing through a conduit 32, 52, 62, 72 of the illustrated system 10. The bubble injection system 110 injects a small portion of an auxiliary fluid into the conduit to form an auxiliary fluid bubble that is trapped between a leading portion of the primary fluid and a trailing portion of the primary fluid. When the primary fluid continues flowing, the primary fluid moves the auxiliary fluid bubble through the conduit, within the bubble detection system 150, at the flow rate to be measured or verified. As explained below, the bubble detection system 150 detects the location of the auxiliary fluid bubble 140 (see FIG. 4B) as a function of time by detecting the detectable characteristic of the auxiliary fluid relative to the primary fluid. By way of example, the auxiliary fluid may transmit a greater amount of radiation or light than does the primary fluid such that the presence of the auxiliary fluid bubble 140, rather than the primary fluid, is represented by a signal peak.

As shown in FIGS. 4A, and 4B, the first preferred bubble injection system 110 is formed from a pair of discrete valves that are interconnected, Valve 1 and Valve 2. In this embodiment, each valve is a three-port, two position valve that has a common port "C" that can be selectively connected to Port A or Port B. The common Port C can be used as an inlet or outlet as desired. Valve 1 is configured with Port C as its input (selectively connected to one of two outputs) and Valve 2 is configured with Port C as its output (selectively connected to one of two inputs).

These types of valves are sometimes regarded as "diverter valves" in that they are often provided as electromagnetic solenoid valves that can be electrically operated by a controller and selectively moved from a normally open connection (e.g. C to A), to a normally closed connection (e.g. C to B), and back again. Here, as suggested by controller block 170, Valve 1 and Valve 2 are controlled to measure the flow rate of the primary flow as further described below.

In the NORMAL FLOW mode, Valve 1 is set with Port C connected to Port A and Valve 2 is set with Port A connected to Port C such that the two valves collectively define a pass-through path. This NORMAL FLOW mode allows the primary flow to pass through Valve 1 and Valve 2 as if the valves were not present.

In the MOMENTARY BUBBLE INJECTION MODE, by contrast, Valve 1 is set with Port C connected to Port B (plugged, e.g. internally or to waste) and Valve 2 is set so that Port B (auxiliary pump 130) is connected to Port C (bubble injection). The auxiliary pump 130 may simply output air. However, it may be desirable to use any other gas, such as argon, carbon dioxide, helium, hydrogen, neon, nitrogen, and oxygen, if such gases provide a more detectable characteristic relative to the primary fluid.

It is only necessary to inject a small portion of the auxiliary fluid. In the prototype, in fact, a simple low-pressure aquarium pump was used as the auxiliary pump 130.

As shown in FIG. 4A, the flow rate measurement system 100 is usually in the NORMAL FLOW position. This is the position where fluid simply flows through the system 100 as if it were not present. However, when commanded to measure the flow rate by the controller 170, the flow rate measurement system 100 is driven, at least once, into the MOMENTARY BUBBLE INJECTION mode of FIG. 4B. In that moment of time, as shown by FIG. 4B, the incoming flow is very briefly diverted when Valve 1 temporarily connects incoming Port C to plugged Port B, and the air pump 130 inserts an air bubble 140 into the outgoing flow when Valve 2 temporarily connects Port B to Port C. The insertion of the bubble 140 happens very quickly.

The presently preferred embodiment 100 further features a bubble detection system 150 that is located downstream of the bubble injection system 110. After injecting the bubble 140 into the primary flow with the valves in the MOMENTARY BUBBLE INJECTION position of FIG. 4B, the flow rate measurement system 100 quickly returns to the NORMAL FLOW position of FIG. 4A and then the primary fluid flow continues, completely unabated. At that point, the unabated flow rate to be measured naturally advances the auxiliary bubble 140 (e.g. an air bubble) through the tubing within the bubble detection system 150.

As shown, the preferred bubble detection system 150 comprises one or more bubble sensors 151, 152, etc. (five are shown), and then in conjunction with the controller 170, the system simply uses suitable electronics to measures how long it takes for the bubble 140 to move to or between the sensors 151, 152, etc. In the preferred embodiment, each bubble sensor is comprised of two or more light sources 151, 152, etc. (e.g. an LED of any desired wavelength) and two or more light or echo detectors 161, 162, etc. (e.g. a diode array or discrete photocells). Echo detection would be particularly suitable for detecting different gas densities in a gas/gas embodiment. Since the light from the light sources 151, 152 must pass through the tube and be modified in some fashion by the primary fluid and by the auxiliary bubble 140, the tube should be suitably transparent or translucent. In the presently preferred operation, the control electronics 170 operates the sensors 151, 152, etc. to determine how long it takes the bubble 140's leading edge, or trailing edge as desired, to move between sensors. It may be possible to measure how long it takes a bubble 140 to move from the bubble injection system 110 to a single sensor, but the preferred system makes a plurality of differential measurements between two successive sensors.

The flow rate is determined by the travel time between two photocells relative to the known volume between them. The system 100 can rapidly determine the bubble's locations as a function of time which, in combination with the known diameter of the tube and therefore the known volume between two marks, mathematically translates to a volumetric flow rate (V/T). Of special significance, the system 100 is useful with the very low flow rates that are often used in an HPLC system 10. And, moreover, there is no need to divert the solvent flow into a volumetric measuring device, a process that may take several minutes or more, causes delay, and may be less accurate than desired.

Second Preferred Embodiment

FIGS. 6A and 6B depict a second preferred embodiment of a flow rate measurement system 100' that uses bubble injection system 110' formed from a single, six-port, two-position valve, labeled "Valve X." These rotary valves are often coupled to electromechanical controllers to rotate the internal valve mechanism clockwise or counterclockwise as desired, under the direction of a suitable controller 170. As shown in FIGS. 6A and 6B, the various Valve X ports are selectively connected to one of two adjacent ports depending on the valve position, e.g. 1-2, 3-4, 5-6 in Position A (Normal Flow), or 1-6, 2-3, 4-5 in Position B (Momentary Bubble Injection Mode via Air Loop Filling).

In this embodiment, a short piece of tubing 111 is coupled between port 6 and port 3 to form a loop that can uniquely pass the primary fluid or receive the auxiliary fluid or air. As shown by the heavier lines in FIG. 6A, when Valve X is in the NORMAL FLOW configuration of Position A, the primary liquid flow to be measured travels into port 4, then out port 3, through the loop 111, into port 6, and out port 5 to the bubble detection system 150. At the same time, as shown by the thinner lines in FIG. 6A, auxiliary fluid from the auxiliary pump 130 (e.g. air) goes separately from port 1 to port 2.

As shown in FIG. 6B, when Valve X is momentarily in the AIR LOOP FILLING configuration of Position B, the air flow from the auxiliary pump 130 goes from port 1 to port 6, through the loop 111, then into port 3, and out port 2. This position is held for only a short moment. As long as this MOMENTARY BUBBLE INJECTION position lasts, the auxiliary fluid from the auxiliary pump 130 flows into the loop 111 and, at the same time, the primary liquid flow from the HLPLC pump (not shown, but see FIG. 3) travels into port 4 and out port 5. For purposes of exaggeration, the bubble 140 is shown at a substantially midway position in the loop 111, but it of course develops very close to port 6 while Valve X is in the MOMENTARY BUBBLE INJECTION position. The system can adjust the length of the bubble 140 by switching slower or faster as desired. Turbulence issues may generate two bubbles 140 (only one is shown). The control software can be programmed to detect anomalies and adjust the bubble creation parameters if two bubbles are detected.

When Valve X returns to the NORMAL FLOW configuration of Position A, the air bubble 140 trapped in the loop 111 will be carried to the bubble detection system 150. And, as before, the pace of the bubble 140 will allow the controller 170 to determine the flow rate of the primary fluid.

Alternative Embodiments

The above-described embodiments 100, 100' were deployed in an LC or liquid chromatography system and, more particularly, in an HPLC system 10 where the primary fluid is a liquid (e.g. solvent 21) that is pumped at high pressure but moves at a very low flow rate and where the auxiliary fluid is a gas (e.g. air). However, a flow rate measurement system according to alternative embodiments of the present invention could be easily deployed to measure the flow rate of a gas (e.g. as in a GC or gas chromatography system). In such case, the auxiliary fluid would preferably be a liquid such that a liquid bubble is injected into a flowing gas. Provided that the pressure of the gas is sufficiently high, the pressure will maintain the liquid or different gas bubble as a discrete unit and functionally move it through a bubble detection system to establish the flow rate of the primary gas.

The above-described embodiments 100, 100' referenced conduit for transporting the fluid as being tubing that is transparent. However, the conduit could comprise any suitable material or form such as, but not limited to, Teflon®, stainless steel, copper, glass, rubber, etc.

The above-described embodiments 100, 100' also involved bubble detection system 150 that used optical sensors 151, 152, etc., that require transparent and/or translucent tubing. A flow rate measurement system according to other embodiments, however, could use different types of sensors, either to account for primary and/or auxiliary fluids that have detectable characteristics that are better suited to the alternative sensors or to account for the use of tubing that is not transparent or translucent. For example, an audio-based technology based on sound wave detection or echo detection could be used in lieu of modulated radiation.

The invention claimed is:

1. A flow rate measurement system for rapidly measuring a flow rate in an analytical instrument having an analytical component, a primary pump that outputs a primary fluid at the flow rate to be measured or verified, and a conduit for transporting fluid to or from the analytical component, the primary fluid output by the primary pump normally flowing within the conduit, the flow rate measurement system comprising:
   an auxiliary pump that outputs an auxiliary fluid having a detectable characteristic that is distinguishable from the primary fluid;
   a bubble injection system that momentarily injects a small portion of the auxiliary fluid into the conduit for forming an auxiliary fluid bubble that is trapped between a leading portion of the primary fluid and a trailing portion of the primary fluid, the primary fluid moving the auxiliary fluid bubble through the conduit at the flow rate to be measured or verified;
   a bubble detection system for measuring the position of the auxiliary fluid bubble as a function of time based on a time of detecting the detectable characteristic of the auxiliary fluid; and
   a controller for converting the measured position of the auxiliary fluid bubble as a function of time into a volumetric flow rate based on a known volume of the conduit.

2. The flow rate measurement system of claim 1 wherein the primary fluid is a liquid and the auxiliary fluid is a gas.

3. The flow rate measurement system of claim 2 wherein the gas is air.

4. The flow rate measurement system of claim 2 wherein the gas is one of argon, carbon dioxide, helium, hydrogen, neon, nitrogen, and oxygen.

5. The flow rate measurement system of claim 1 wherein the primary fluid is a liquid and the auxiliary fluid is a liquid.

6. The flow rate measurement system of claim 1 wherein the primary fluid is a gas and the auxiliary fluid is a gas.

7. The flow rate measurement system of claim 1 wherein the primary fluid is a gas and the auxiliary fluid is a liquid.

8. The flow rate measurement system of claim 1 wherein the bubble injection system momentarily prevents the primary fluid from flowing within the conduit, injects a small portion of the auxiliary fluid into the conduit, and then permits the primary fluid to continue flowing within the conduit, the small portion of auxiliary fluid forming an auxiliary fluid bubble that is trapped between a leading portion of the primary fluid and a trailing portion of the primary fluid, and when flowing, the primary fluid moving the auxiliary fluid bubble through the conduit at the flow rate to be measured or verified.

9. The flow rate measurement system of claim 8 wherein the bubble injection system comprises:
   a first valve comprising a three-port, two-position valve that is configured to provide a common input port in fluid communication with the primary pump and first and second output ports that are selectively connected to the common input port and respectively comprise a capped output port and a normal flow output port;
   a second valve comprising a three-port, two-position valve that is configured to provide a common output port and first and second input ports that are selectively connected to the common output port and respectively comprise an auxiliary fluid input port and a normal flow input port, the auxiliary fluid input port in fluid communication with the auxiliary pump and the normal flow input port in fluid communication with the first valve's normal flow output port; and a control system for causing the first and second valves to move from a normal flow position that permits the primary fluid to flow into the common input port, out the normal flow output port, into the normal flow input port, and out the common output port, to a momentary bubble injection position that momentarily blocks the primary fluid by connecting the common input to the capped output port and momentarily permits the auxiliary fluid to flow into the auxiliary fluid input port and out the common output port to inject the small portion of the auxiliary fluid into the conduit, and back to the normal flow position, to form the auxiliary fluid bubble.

10. The flow rate measurement system of claim 1 wherein the bubble injection system comprises:

a valve comprising a six-port, two-position valve configured to have an input port in fluid communication with the primary pump, an output port, and first loop port, a second loop port, an auxiliary pump input port in fluid communication with the auxiliary pump, and an exhaust port;

a fluid loop connected to the first and second loop ports, the fluid loop selectively being a straight pass-through of primary fluid and a momentary recipient of auxiliary fluid; and a control system for causing the valve to move from a normal flow position that permits the primary fluid to flow into the input port, out one of the loop ports, through the fluid loop, in the other one of the loop ports, and out the output port, to a momentary bubble injection position that momentarily connects the input port directly to the output port and momentarily permits auxiliary fluid to flow into the auxiliary fluid input port, out one of the loop ports, through the fluid loop, in the other one of the loop ports, and out the exhaust port to inject the small portion of the auxiliary fluid into the conduit, and back to the normal flow position, to form the auxiliary fluid bubble.

11. A flow rate measurement system for rapidly measuring a flow rate in an analytical instrument having an analytical component, comprising:

a primary pump that outputs a primary fluid at the flow rate to be measured or verified;

a conduit for transporting fluid to or from the analytical component, the primary fluid output by the primary pump normally flowing within the conduit;

an auxiliary pump that outputs an auxiliary fluid having a detectable characteristic that is distinguishable from the primary fluid;

a bubble injection system that momentarily, injects a small portion of the auxiliary fluid into the conduit for forming an auxiliary fluid bubble that is trapped between a leading portion of the primary fluid and a trailing portion of the primary fluid, the primary fluid moving the auxiliary fluid bubble through the conduit at the flow rate to be measured or verified;

a bubble detection system for measuring the position of the auxiliary fluid bubble as a function of time based on a time of detecting the detectable characteristic of the auxiliary fluid; and a controller for converting the measured position of the auxiliary fluid bubble as a function of time into a volumetric flow rate based on a known volume of the conduit.

12. The flow rate measurement system of claim 11 wherein the primary fluid is a liquid and the auxiliary fluid is a gas.

13. The flow rate measurement system of claim 12 wherein the gas is air.

14. The flow rate measurement system of claim 12 wherein the gas is one of argon, carbon dioxide, helium, hydrogen, neon, nitrogen, and oxygen.

15. The flow rate measurement system of claim 11 wherein the primary fluid is a gas and the auxiliary fluid is a liquid.

16. The flow rate measurement system of claim 11 wherein the bubble injection system momentarily prevents the primary fluid from flowing within the conduit, injects a small portion of the auxiliary fluid into the conduit, and then permits the primary fluid to continue flowing within the conduit, the small portion of auxiliary fluid forming an auxiliary fluid bubble that is trapped between a leading portion of the primary fluid and a trailing portion of the primary fluid, and when flowing, the primary fluid moving the auxiliary fluid bubble through the conduit at the flow rate to be measured or verified.

17. The flow rate measurement system of claim 16 wherein the bubble injection system comprises:

a first valve comprising a three-port, two-position valve that is configured to provide a common input port in fluid communication with the primary pump and first and second output ports that are selectively connected to the common input port and respectively comprise a capped output port and a normal flow output port;

a second valve comprising a three-port, two-position valve that is configured to provide a common output port and first and second input ports that are selectively connected to the common output port and respectively comprise an auxiliary fluid input port and a normal flow input port, the auxiliary fluid input port in fluid communication with the auxiliary pump and the normal flow input port in fluid communication with the first valve's normal flow output port; and a control system for causing the first and second valves to move from a normal flow position that permits the primary fluid to flow into the common input port, out the normal flow output port, into the normal flow input port, and out the common output port, to a momentary bubble injection position that momentarily blocks the primary fluid by connecting the common input to the capped output port and momentarily permits the auxiliary fluid to flow into the auxiliary fluid input port and out the common output port to inject the small portion of the auxiliary fluid into the conduit, and back to the normal flow position, to form the auxiliary fluid bubble.

18. The flow rate measurement system of claim 11 wherein the bubble injection system comprises:

a valve comprising a six-port, two-position valve configured to have an input port in fluid communication with the primary pump, an output port, and first loop port, a second loop port, an auxiliary pump input port in fluid communication with the auxiliary pump, and an exhaust port;

a fluid loop connected to the first and second loop ports, the fluid loop selectively being a straight pass-through of primary fluid and a momentary recipient of auxiliary fluid; and a control system for causing the valve to move from a normal flow position that permits the primary fluid to flow into the input port, out one of the loop ports, through the fluid loop, in the other one of the loop ports, and out the output port, to a momentary bubble injection position that momentarily connects the input port directly to the output port and momentarily permits auxiliary fluid to flow into the auxiliary fluid input port, out one of the loop ports, through the fluid loop, in the other one of the loop ports, and out the exhaust port to inject the small portion of the auxiliary fluid into the conduit, and back to the normal flow position, to form the auxiliary fluid bubble.

* * * * *